United States Patent [19]

Combe et al.

[11] Patent Number: 5,141,560
[45] Date of Patent: Aug. 25, 1992

[54] DENTAL CEMENT

[75] Inventors: Edward C. Combe, Altrincham; Ben C. Cohen, Prestwich; Alan D. Wilson, Liphook, all of England

[73] Assignee: National Research Development Corporation, London, England

[21] Appl. No.: 659,496

[22] Filed: Nov. 28, 1990

[30] Foreign Application Priority Data

Dec. 1, 1989 [GB] United Kingdom ................ 8927158
Jun. 13, 1990 [GB] United Kingdom ................ 9013165

[51] Int. Cl.$^5$ .............................................. C09K 3/00
[52] U.S. Cl. ..................................... 106/35; 433/228.1
[58] Field of Search ........................................... 106/35

[56] References Cited

U.S. PATENT DOCUMENTS

| | | | |
|---|---|---|---|
| 3,509,089 | 4/1970 | Dougherty | 106/35 |
| 4,064,629 | 12/1977 | Stoner et al. | 106/35 |
| 4,773,933 | 9/1988 | Futami et al. | 106/35 |

FOREIGN PATENT DOCUMENTS 2110655 9/1971 Fed. Rep. of Germany .
1213210 8/1989 Japan .

*Primary Examiner*—William R. Dixon, Jr.
*Assistant Examiner*—Margaret V. Einsmann
*Attorney, Agent, or Firm*—Nixon & Vanderhye

[57] ABSTRACT

Dental cement comprising (a) calcium or zinc oxide or hydroxide, (b) a substituted aromatic compound capable of forming a cement with (a), the calcium or zinc oxide or hydroxide of (a) being in stoichiometric excess over (b), and (c) dry poly(carboxylic acid), or a precursor thereof, or dry cation-crosslinkable polymeric acid containing on average 1 phosphonic acid group per 1 to 3 backbone carbon atoms. The cement has bacteriostatic properties, stimulates the formation of secondary dentine, forms an adhesive bond and can be used where pulp tissue is exposed.

9 Claims, No Drawings

DENTAL CEMENT

This invention relates to a dental cement.

Dental cements are known which comprise an oxide of a divalent metal which reacts with a non-aqueous fluid. One such dental cement is zinc oxide-eugenol, widely used for temporary restorations but this cannot be used directly where pulp tissue is exposed. Another such material is a lining cement comprising calcium hydroxide and a salicylate compound. This latter material is an effective bacteriostat because it releases strongly alkaline oxide which cauterises any exposed pulp tissue and stimulates the formation of secondary dentine. Unfortunately, this material does not form an adhesive bond and also is liable to eventual dissolution, thus forming a void instead of a lining under the restoration and potentially weakening the total strength of the restoration.

It would be desirable to retain the bacteriostatic property of these lining cements while increasing their adhesion and their durability.

According to the present invention, a dental cement comprises (a) calcium or zinc oxide or hydroxide in stoichiometric excess over (b), (b) a substituted aromatic (preferably phenolic) compound preferably an ortho difunctional phenol (such as o-methoxy-phenol (eugenol)) or an ester of a polyhydric alcohol and salicylic acid capable of forming a cement with (a), and (c) dry poly(carboxylic acid) (or precursor thereof as herein defined) or dry cation-crosslinkable polymeric acid containing on average one phosphonic acid group per one to three backbone carbon atoms.

Optional additional components include any one or more of (d) zinc oxide unless already present as (a) and/or an ion-leachable glass.

(e) a chelating agent such as tartaric acid, tetrahydrofuran tetracarboxylic acid or citric acid, (f) an inert filler such as silica, alumina or titanium dioxide, and (g) water, optionally mixed with another component, e.g. forming a paste with (a) (c) (d) or (f) or dissolving (e).

The preferred poly(carboxylic acid)s suitable for use as (c) are those prepared by the homopolymerisation and copolymerisation of unsaturated aliphatic carboxylic acids for example aconitic acid, acrylic acid, citraconic acid, fumaric acid, glutaconic acid, itaconic acid, maleic acid, mesaconic acid, methacrylic acid, 3-butene 1,2,3 tricarboxylic acid and tiglic acid; and the copolymerisation of these acids with other unsaturated aliphatic monomers for example vinyl monomers, such as vinyl hydrocarbon monomers, vinyl ethers, acrylamide or acrylonitrile. Particularly preferred are the homopolymers of acrylic acid and its copolymers with one or more of aconitic, fumaric, itaconic, maleic, mesaconic, methacrylic, muconic or tiglic acid, particularly copolymers of acrylic acid and itaconic acid. Especially preferred are homopolymers of acrylic acid. Good results are also possible using copolymers of vinyl methyl ether and maleic acid.

It is also possible to use a precursor of a poly(carboxylic acid) as (i); as used in this specification, "precursor" means a polymer which will be transformed into the poly(carboxylic acid); furthermore, polyacrylic acids may be prepared by hydrolysis of corresponding polyacrylonitriles. The precursor of a poly(carboxylic acid) may be a homopolymer of an unsaturated carboxylic acid anhydride or a copolymer with an above mentioned other carboxylic acid or anhydride thereof; or a copolymer of an unsaturated carboxylic acid anhydride with an unsaturated aliphatic monomer, for example vinyl monomers, such as vinyl hydrocarbon monomers, vinyl ethers, acrylamide or acrylonitrile. Good results may be obtained by using homopolymers of maleic anhydride or vinyl orthophthalic anhydride, or copolymers thereof, especially block copolymers thereof, with ethylene, propylene, butenes, styrene and vinyl methyl ether.

The poly(carboxylic acid) or precursor thereof is preferably linear, although branched polymers may also be used. Preferably, the polymer has an average molecular weight from 1,000 to 1,000,000, more preferably from 1,500 to 250,000, and most preferably from 15,000 to 100,000. In this specification the average molecular weight is defined as being that measured by ultracentrifuging.

The component (d) may comprise zinc oxide. Alternatively, or in addition thereto, it may comprise a silicate or an aluminosilicate. The preferred particulate ion-leachable silicated or (fluoro)aluminosilicates are glasses wherein the ratio by weight of acidic to basic oxides in the glass is such that the glass will react with (c) in the presence of water to set the latter. By "(fluoro)aluminosilicate" is meant herein fluoroaluminosilicate or aluminosilicate. The principal acidic oxide in the aluminosilicate glass is a silica, although the glass may also contain minor amounts of other anhydrides such as phosphorous pentoxide and boric oxide. The principal basic oxide in the glass is alumina which, although it has amphoteric properties, can be considered for the purposes of the present invention solely as a basic oxide. Particularly preferred aluminosilicate glasses fall within the composition range of 10 to 65% w/w silica and 15 to 50% w//w alumina.

The aluminosilicate glass desirably contains at least one other basic oxide, preferably calcium oxide, which may be present in the glass composition in an amount from 0 to 50% w/w. The calcium oxide may be partly or wholly replaced by sodium oxide or other basic oxide such as strontium oxide or barium oxide or a mixture of basic oxides, although in some applications the presence of sodium oxide may be undesirable as this oxide tends to increase the solubility of the resulting cement. Preferred glasses for use in the present invention containing alumina, silica and calcium oxide are the gehlenite and anorthite glasses, and in general glasses falling within the composition rate 10 to 65% w/w silica, 15 to 50% w/w alumina and 0 to 50% w/w calcium oxide.

Other aluminosilicate glasses suitable for use in the present invention may contain fluoride, suitably up to 15% by weight preferably less than 10% by weight. A class of fluoroaluminosilicate glasses particularly suited to dental applications are those wherein the ratio by weight of silica to alumina is from 1.5 to 2.0 and the ratio by weight of fluorine to alumina is from 0.6 to 2.5; or those wherein the ratio by weight of silica to alumina is from 0.5 to 1.5 and the ratio by weight of fluorine to alumina is from 0.25 to 2.0.

Particularly preferred glasses are those wherein the glass has a composition within the following systems:

$CaO-Al_2O_3-SiO_2$;  (a)

$CaO-Al_2O_3-SiO_2-CaF_2$;  (b)

$CaF_2-Al_2O_3-SiO_2$;  (c)

$CaF_2-Al_2O_3-SiO_2-AlPO_4$;  (d) or $CaF_2-Al_2O_3-SiO_2-AlPO_4-AlF_3-Na_3AlF_6$  (e)

The solid components used in the present invention are preferably powdered to a degree of fineness which produces a smooth cement paste when mixed and which sets within a reasonable time, e.g. particles sieved through 0.1 mm mesh.

The invention will now be described by way of example.

EXAMPLE 1

A first paste was compounded as follows:
2.11 g: 1,3 butylene glycol disalicylate
1.57 g: calcium phosphate
0.88 g: calcium tungstate
0.50 g: freeze-dried poly(acrylic acid)(MW=49000)
0.43 g: zinc oxide The first component was a liquid and the remainder were solids, ground to a particle size not exceeding 0.05 mm.

A second paste was compounded as follows:
2.54 g: calcium hydroxide
1.74 g: ethyl toluol sulphonamide
0.50 g: freeze-dried poly(acrylic acid)(MW=49000)
0.46 g: zinc oxide
0.24 g: titanium dioxide The sulphonamide was a liquid and the other components of the second paste were solids ground to a particle size not exceeding 0.05 mm.

The two pastes were thoroughly mixed together and placed in a dry mould and stored under oral conditions of humidity and temperature. Further samples of the mixed pastes were studied "wet" (under water at 37° C.) and "dry" (in an electric oven at 37° C.), with the following results:

pH of mixed paste: 10.5
Working time: 6½ minutes
Setting time: 4¼ minutes
diametral tensile strength (MPa):

|  | After 1 day | 1 week | 1 month |
| --- | --- | --- | --- |
| Wet | 2.1 | 2.5 | 2.9 |
| Oral | 3.3 | 3.5 | 3.5 |
| Dry | 3.5 | 4.9 | 4.2 |

EXAMPLE 2

A first paste was compounded as follows:
687 mg: 1,3 butylene glycol disalicylate
510 mg: calcium phosphate
396 mg: strontium aluminofluorosilicate glass (24.5% $Al_2O_3$, 32% $SiO_2$, 28.7% SrO, 13%F, 5% phosphate)
286 mg: calcium tungstate
100 mg: freeze-dried poly(acrylic acid)(MW=49000)
141 mg: zinc oxide The first component was a liquid and the remainder were solids, ground to a particle size not exceeding 0.05 mm.

A second paste was compounded as follows:
829 mg: calcium hydroxide
566 mg: ethyl toluol sulphonamide
396 mg: strontium aluminofluorosilicate glass (as in the first paste)
100 mg: freeze-dried poly(acrylic acid)(MW=49000)
149 mg: zinc oxide
77 mg: titanium dioxide
8 mg: tartaric acid The sulphanomide was a liquid and the other components of the second paste were solids ground to a particle size not exceeding 0.05 mm.

The two pastes were thoroughly mixed together and placed in a dry mould and stored under oral conditions of humidity and temperature. Further samples of the mixed pastes were studied "wet" (under water at 37° C.) and "dry" (in an electric oven at 37° C., with the following results:

pH of mixed paste: 11.6
Working time: 4¾ minutes
Setting time: 3¼ minutes
Diametric tensile strength (MPa):

|  | After 1 day | 1 week | 1 month |
| --- | --- | --- | --- |
| Wet | 2.8 | 2.9 | 1.9 |
| Oral | 4.4 | 2.6 | 4.4 |
| Dry | 3.6 | 3.9 | 4.4 |

In both Examples, the adhesion of the set paste to dentine was about half that of a set glass polyalkenoate cement to dentine, in other words still adequate for all reasonable purposes. By comparison, as already mentioned, conventional calcium hydroxide lining cements show practically no adhesion.

A number of reactions and processes occur in the above cements:

1. On mixing such components, the $Ca(OH)_2$ and salicylate form a first system giving a set product in a non-aqueous system, by the formation of a calcium salicylate.
2. Because the calcium hydroxide is in stoichiometric excess, it gives the material a high initial pH which is known clinically to be essential for stimulating the formation of secondary dentine.
3. In the clinical situation, water, which is invariably present in the tooth dentine even if not added deliberately as a cement component, can diffuse into the mixture, and this accelerates reaction 1.
4. Water which diffuses into the mixture also begins to dissolve the poly(acrylic acid) or analogous compounds. This promotes adhesion of the product to tooth dentine.
5. The dissolved polymeric carboxylic acid (forming a second system) can react with some of the excess calcium hydroxide, yielding a cross-linked calcium polyacrylate salt. This can make a contribution to the development of improved mechanical properties in the material over a period of time.
6. Similarly, the polymeric carboxylic acid may react with the zinc oxide or ion-leachable glass, if present, to give enhanced mechanical properties over a period of time.
7. If present and of appropriate composition, the ion-leachable glass releases fluoride ions, which can diffuse to the surrounding tooth tissue, with known clinical benefit.
8. Unreacted ion-leachable glass if present may have a reinforcing effect on the set material.

9. The reactions 3-7 which depend on the diffusion of water into the cement (that is, the development of adhesive and strength properties, and release of fluoride ions) may be enhanced if this cement subsequently has a water based cement (such as a glass-ionomer) placed on top of it.

This cement has a number of important clinical applications:

A. Pulp capping materials (when pulp is obviously exposed).

B. Liners or subliners under tooth restorative materials such as polyalkenoates, polymer-ceramic composites and dental amalgam (see point 9 above).

(Note particularly that this cement is thus suitable for placing on pulp and on dentine, whichever is/are present, and prior cements did not have this versatility.)

C. Root canal cement sealers.

D. Periodontal dressing materials.

This cement therefore offers the advantages of clinical versatility and reduction of clinician's stocks (separate materials for A and B being redundant); increase in the available dentine-adhesive area without sacrificing the known clinical benefits of $Ca(OH)_2$ (placing of which had diminished the available adhesive area); and improvement in strength since this cement does not disappear leaving a void as $Ca(OH)_2$ pulp capping materials tended to do.

We claim:

1. A dental cement, comprising the following components:

(a) calcium or zinc oxide or hydroxide;

(b) a substituted aromatic compound capable of forming a cement with component (a), component (a) being in stoichiometric excess over component (b); and (c) a dry poly (carboxylic acid), a precursor transformable into said dry poly(carboxylic acid), or a dry cation-crosslinkable polymeric acid containing on average one phosphonic acid group per one to three backbone carbon atoms.

2. A dental cement according to claim 1, wherein component (b) is a phenolic compound.

3. A dental cement according to claim 2, wherein component (b) is an ortho difunctional phenol.

4. A dental cement according to claim 1, wherein component (b) is an ester of a polyhydric alcohol and salicylic acid.

5. A dental cement according to claim 1, and further comprising a component selected from the group consisting of:

(d) zinc oxide unless already present as component (a);

(e) an ion-leachable glass;

(f) a chelating agent;

(g) an inert filler; and (h) water.

6. A dental cement according to claim 5, wherein said chelating agent (f) is tartaric acid, tetrahydrofuran tetracarboxylic acid or citric acid.

7. A dental cement according to claim 5, wherein said inert filler (g) is silica, alumina or titanium dioxide.

8. A dental cement according to claim 5, wherein said water (h) is mixed with a component selected from the group consisting of components (a), (b), (c), (d), (e), (f) and (g).

9. A dental cement according to claim 8, wherein the water (h) forms a paste with component (a), (c), (d), (e) or (g) or dissolves component (f).

* * * * *